United States Patent
Rim et al.

(10) Patent No.: US 10,281,410 B2
(45) Date of Patent: May 7, 2019

(54) SYSTEMS AND METHODS OF TESTING SEMICONDUCTOR DEVICES USING SIMULTANEOUSLY SCANNING OF A PLURALITY OF REGIONS THEREIN AND METHODS OF FORMING SEMICONDUCTOR DEVICES USING THE SAME

(71) Applicant: Samsung Electronics Co., Ltd., Suwon-si, Gyeonggi-do (KR)

(72) Inventors: Min Ho Rim, Hwaseong-si (KR); Yu Sin Yang, Seongnam-si (KR); Chung Sam Jun, Suwon-si (KR); Yun Jung Jee, Seongnam-si (KR)

(73) Assignee: SAMSUNG ELECTRONICS CO., LTD., Samsung-ro, Yeongtong-gu, Suwon-si, Gyeonggi-do (KR)

(*) Notice: Subject to any disclaimer, the term of this patent is extended or adjusted under 35 U.S.C. 154(b) by 0 days.

(21) Appl. No.: 15/867,070

(22) Filed: Jan. 10, 2018

(65) Prior Publication Data
US 2018/0356349 A1    Dec. 13, 2018

(30) Foreign Application Priority Data
Jun. 8, 2017    (KR) .......................... 10-2017-0071303

(51) Int. Cl.
*G01N 21/95*    (2006.01)
*H01L 21/67*    (2006.01)
*H01L 21/66*    (2006.01)

(52) U.S. Cl.
CPC ... *G01N 21/9501* (2013.01); *H01L 21/67288* (2013.01); *H01L 22/12* (2013.01)

(58) Field of Classification Search
CPC .......... G01N 21/9501; H01L 21/67288; H01L 22/12
See application file for complete search history.

(56) References Cited

U.S. PATENT DOCUMENTS 5,191,200 A  *  3/1993  van der Werf ....... G02B 21/241
                                                       250/201.4
8,614,415 B2 * 12/2013  Moribe ................ G01N 21/956
                                                         250/225

(Continued)

FOREIGN PATENT DOCUMENTS

JP      2016529519       9/2016
KR      10-0853148       8/2008

(Continued)

OTHER PUBLICATIONS

Attota, et al.; *Nanometrology using Through-focus Scanning Optical Microscopy Method*; Measurement Science and Technology, vol. 22, pp. 02402 (2011); 12 pages.

(Continued)

*Primary Examiner* — Tri T Ton
(74) *Attorney, Agent, or Firm* — Muir Patent Law, PLLC

(57) ABSTRACT

A method of testing can include providing a first beam having a first focal length and a second beam having a second focal length that is less than the first focal length to a stage region to provide a first reflected beam and a second reflected beam from the stage region. The first reflected beam can be detected among the first reflected beam and the second reflected beam reflected from the stage region. The second reflected beam can be detected among the first reflected beam and the second reflected beam reflected from the stage region. A first image can be generated from the first reflected beam and a second image can be generated from the second reflected beam. The first image and the second image can be combined to provide a 3D image.

17 Claims, 15 Drawing Sheets

(56) References Cited

U.S. PATENT DOCUMENTS

| | | | |
|---|---|---|---|
| 9,513,112 B1 | 12/2016 | Rush et al. | |
| 9,741,954 B2 | 8/2017 | Bruder et al. | |
| 9,746,426 B2* | 8/2017 | Amanullah | G01N 21/9501 |
| 2012/0013899 A1* | 1/2012 | Amanullah | G01N 21/9501 |
| | | | 356/237.5 |
| 2014/0300890 A1 | 10/2014 | Lange et al. | |
| 2016/0209334 A1* | 7/2016 | Chen | G01N 21/8851 |
| 2016/0214107 A1 | 7/2016 | Viasnoff et al. | |
| 2016/0301915 A1 | 10/2016 | Shechtman et al. | |
| 2017/0003230 A1 | 1/2017 | Park et al. | |
| 2017/0237926 A1 | 8/2017 | Bruder et al. | |

FOREIGN PATENT DOCUMENTS

| | | |
|---|---|---|
| KR | 101507950 | 4/2015 |
| KR | 20160019439 | 2/2016 |
| KR | 101652355 | 8/2016 |
| WO | WO 2015080480 | 6/2015 |

OTHER PUBLICATIONS

Abrahamsson, et al; *MultiFocus Polarization Microscope (MF-PolScope) for 3D Polarization Imaging of Up to 25 Focal Planes Simultaneously*; Optics Express; vol. 23, No. 6; pp. 7734-7754 (2015); 21 Pages.

Lee et al; *Tip/Tilt-Compensated Through-Focus Scanning Optical Microscopy*; Proceedings vol. 10023, Optical Metrology and Inspection for Industrial Applications IV; 100230P; Event: SPIE/COS Photonics Asia; (2016) Beijing, China (1 page).

\* cited by examiner

SYSTEMS AND METHODS OF TESTING SEMICONDUCTOR DEVICES USING SIMULTANEOUSLY SCANNING OF A PLURALITY OF REGIONS THEREIN AND METHODS OF FORMING SEMICONDUCTOR DEVICES USING THE SAME

CROSS-REFERENCE TO RELATED APPLICATIONS

This application claims the benefit of Korean Patent Application No. 10-2017-0071303, filed on Jun. 8, 2017, in the Korean Intellectual Property Office, the disclosure of which is incorporated herein in its entirety by reference.

FIELD

The present inventive concept relates to a test system, a test method, and a method of fabricating a semiconductor device using the test system and the test method.

BACKGROUND

Due to the miniaturization of semiconductor devices, vertically structured semiconductor devices are being produced. Therefore, there is a need for a technique for testing such a vertically structured semiconductor device to find a defect in such semiconductor devices.

SUMMARY

Embodiments according to the inventive concept can provide systems and methods of testing semiconductor devices using simultaneously scanning of a plurality of regions therein and methods of forming semiconductor devices using the same. Pursuant to these embodiments of the inventive concept, a method of testing can include providing a first beam having a first focal length and a second beam having a second focal length that is less than the first focal length to a stage region to provide a first reflected beam and a second reflected beam from the stage region. The first reflected beam can be detected among the first reflected beam and the second reflected beam reflected from the stage region. The second reflected beam can be detected among the first reflected beam and the second reflected beam reflected from the stage region. A first image can be generated from the first reflected beam and a second image can be generated from the second reflected beam. The first image and the second image can be combined to provide a 3D image.

In some embodiments according to the inventive concept, a test system can include an incident optics configured to provide a first beam having a first focal length and a second beam having a second focal length that is less than the first focal length. A stage region can be configured to support a semiconductor wafer, the stage region positioned to receive the first and second beams and to provide a first reflected beam and a second reflected beam to the incident optics responsive to the first and second beams. A first light detector can be configured to detect the first reflected beam among the first and second reflected beams reflected from the stage region to the first light detector through the incident optics. A second light detector can be configured to detect the second reflected beam among the first and second reflected beams reflected from the stage region to the second light detector through the incident optics. An image processor can be configured to receive the first reflected beam from the first light detector and the second reflected beam from the second light detector and configured to generate a three-dimensional (3D) image based on the first and second reflected beams provided by the first and second light detectors, respectively.

In some embodiments according to the inventive concept, a method of fabricating a semiconductor device can include providing a first semiconductor device including at least one layer, the first semiconductor device on a first semiconductor wafer and performing a first test on the first semiconductor device, where the performing the first test can include providing a first beam with a first focal length to a first test region of the first semiconductor device to provide a first reflected beam from the first test region responsive to the first beam. A second beam can be provided with a second focal length less than the first focal length to a second test region of the first semiconductor device to provide a second reflected beam from the second test region responsive to the second beam, wherein the second test region is disposed between an upper surface of the first semiconductor device and the first test region. The first reflected beam and the second reflected beam can be detected among beams reflected from the first semiconductor device and a 3D image can be generated using the first reflected beam and the second reflected beam.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE EMBODIMENTS

Embodiments according to the inventive concept are described hereinafter with reference to the accompanying drawings. The inventive concept may, however, be embodied in many different forms and should not be construed as limited to the embodiments set forth herein. Rather, these embodiments are provided so that this disclosure will be thorough and complete, and will fully convey the scope of the present inventive subject matter to those skilled in the art. Like numbers refer to like elements throughout.

Hereinafter, a test system according to embodiments will be described.

Figure 1:
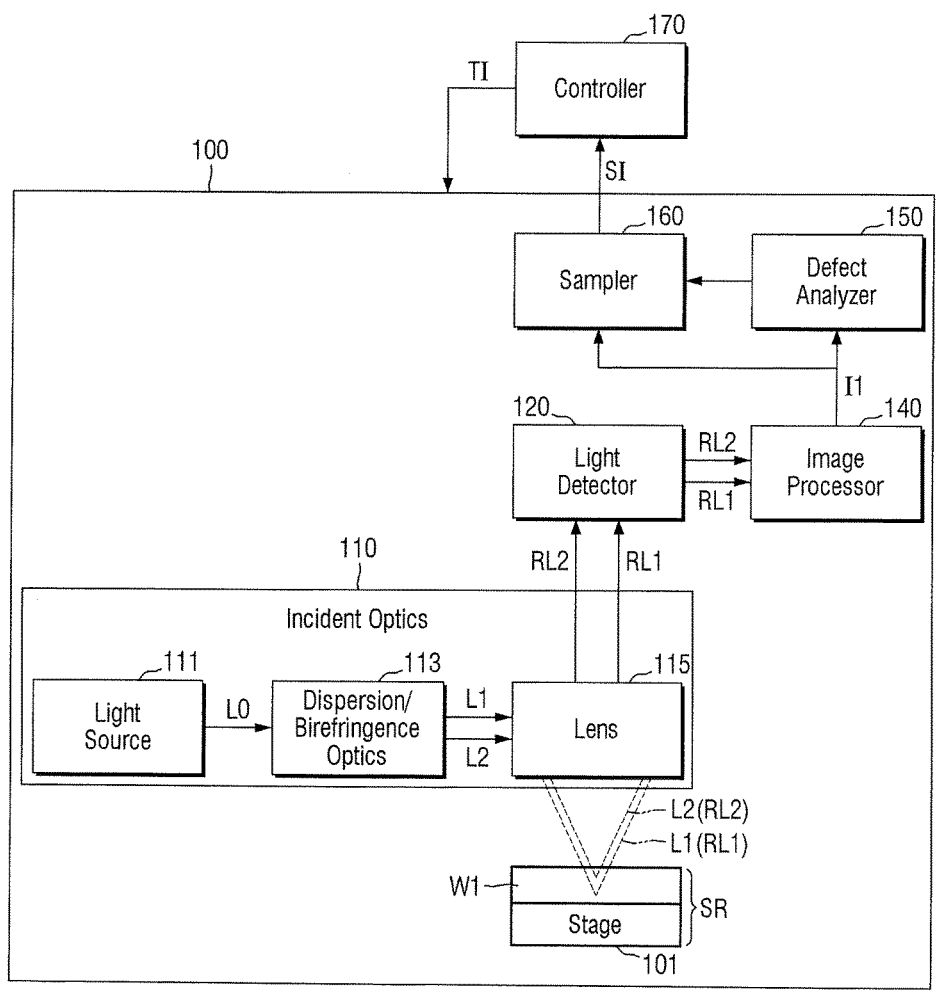
FIG. 1 is a block diagram of a test system in some embodiments according to the inventive concept.

FIG. 1 is a block diagram of a test system 100 according to embodiments.

Referring to FIG. 1, the test system 100 in some embodiments according to the inventive concept may include incident optics 110, a stage region SR, a light detector 120, an image processor 140, a defect analyzer 150, and a sampler 160. In some embodiments, a controller 170 may not be included in the test system 100, however, in some embodiments, the controller 170 may be disposed in the test system 100. It will be understood that is some embodiments according to the inventive concept, the term "light" can mean any electromagnetic radiation that is adaptable for use in the test system 100. It will be further understood that the term "beam" can be used to refer to a beam of light, as defined herein.

The stage region SR may include a stage 101 which can accommodate a first semiconductor wafer W1 that is to be tested by the test system 100.

Figure 2A:
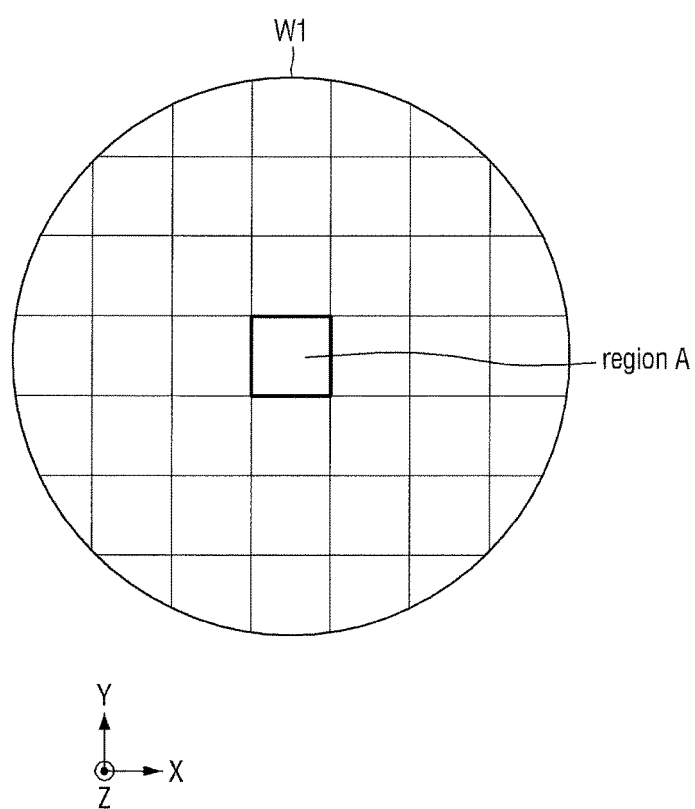
FIG. 2A illustrates a first semiconductor wafer on which the test system of FIG. 1 performs a first test.
Figure 2B:
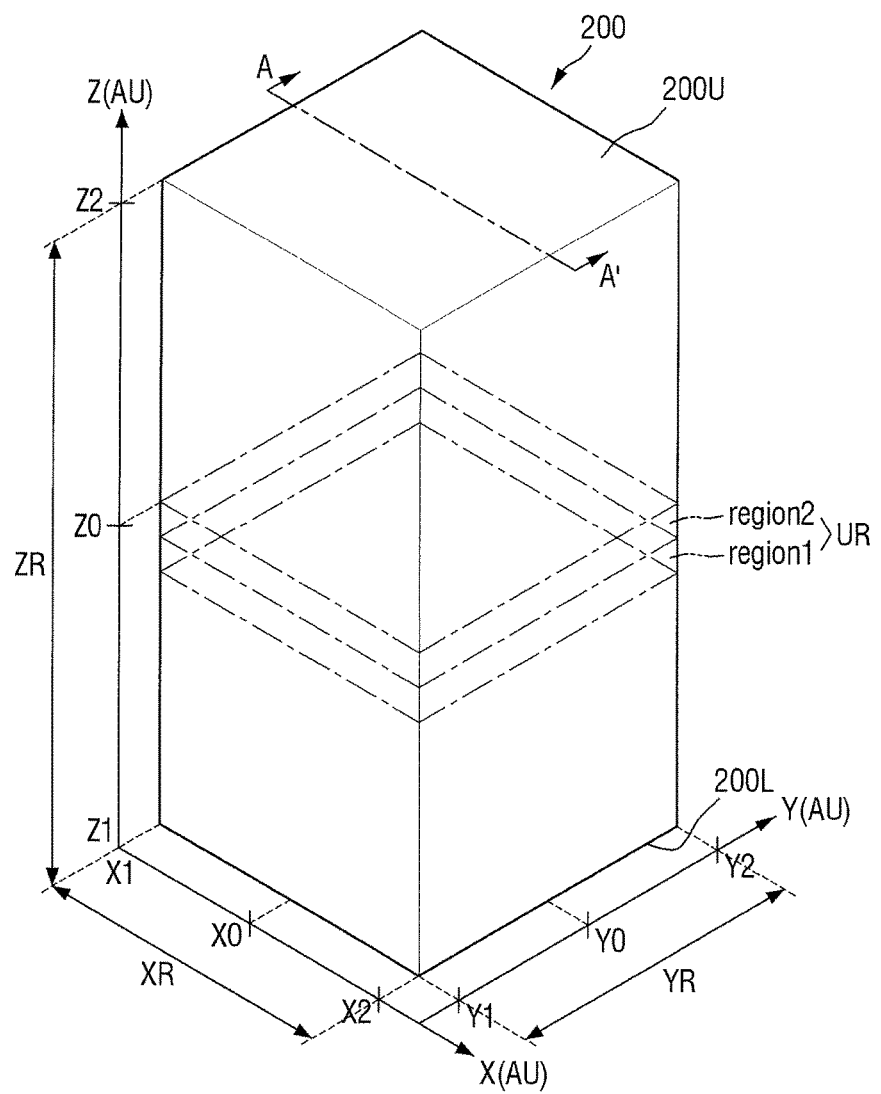
FIG. 2B is a diagram for explaining embodiments relating to a test region on which the first test is performed.

FIG. 2A illustrates the first semiconductor wafer W1 on which the test system 100 of FIG. 1 can perform a first test. FIG. 2B is a diagram for explaining embodiments relating to a test region on which the first test is performed.

Referring to FIG. 2A, the first semiconductor wafer W1 may include a plurality of regions arranged along an X-axis direction and a Y-axis direction. The X-axis direction and the Y-axis direction may be directions intersecting each other.

The regions of the first semiconductor wafer W1 may include region A. In each of the regions including region A, for example, a semiconductor device may be formed. In some embodiments, the semiconductor device formed in each of the regions of the first semiconductor wafer W1 may be subsequently packaged.

Specifically, referring to FIG. 2B, a first semiconductor device 200 may be a semiconductor device formed in region A of the first semiconductor wafer W1. The test system 100 of FIG. 1 may perform the first test on the first semiconductor device 200. The units of an X-axis, a Y-axis and a Z-axis of a coordinate system illustrated in FIG. 2B may be arbitrary unit (AU).

The first semiconductor device 200 may extend by a first range XR along the X-axis direction, extend by a second range YR along the Y-axis direction, and extend by a third range ZR along the Z-axis direction. The Z-axis direction may be a direction intersecting the X-axis direction and the Y-axis direction. In the first test, the test system 100 may scan the first semiconductor device 200 by the first range XR in the X-axis direction, by the second range YR in the Y-axis direction, and by the third range ZR in the Z-axis direction. That is, in the first test, the entire region of the first semiconductor device 200 may be scanned.

The first range XR may be an X-axis coordinate range of the first semiconductor device 200 extending along the X-axis direction. The first semiconductor device 200 may extend along the X-axis direction by a range from X1 (AU) to X2 (AU). For example, when X0 (AU) is 0 (AU), X1 may be −2 (AU) and X2 may be +2 (AU). In this case, XR may be a range of −2 (AU) to +2 (AU). For example, each of X1 (AU), X0 (AU), and X2 (AU) may be a respective integer.

The second range YR may be a Y-axis coordinate range of the first semiconductor device 200 extending along the Y-axis direction. The first semiconductor device 200 may extend along the Y-axis direction by a range from Y1 (AU) to Y2 (AU). For example, when Y0 (AU) is 0 (AU), Y1 may be −2 (AU), and Y2 may be +2 (AU). In this case, the second range YR may be a range of −2 (AU) to +2 (AU). For example, each of Y1 (AU), Y0 (AU), and Y2 (AU) may a respective integer.

The third range ZR may be a Z-axis coordinate range of the first semiconductor device 200 extending along the Z-axis direction. The first semiconductor device 200 may extend along the Z-axis direction by a range from Z1 (AU) to Z2 (AU). For example, when Z0 (AU) is 0 (AU), Z1 may be −4 (AU), and Z2 may be +4 (AU). In this case, the third range ZR may be a range of −4 (AU) to +4 (AU). For example, each of Z1 (AU), Z0 (AU), and Z2 (AU) may be a respective integer.

The first semiconductor device 200 may include a lower surface 200L and an upper surface 200U. The position of the lower surface 200L of the first semiconductor device 200 on Z-axis coordinates may be Z1 (AU). The position of the upper surface 200U of the first semiconductor device 200 on the Z-axis coordinates may be Z2 (AU).

The test system 100 may test a unit region UR each time. While the test system 100 is testing the unit region UR once, the incident optics 110 may emit a beam toward the stage region SR once.

The unit region UR may include a first test region region1 and a second test region region2. The first test region region1 and the second test region region2 may be separated from one another along the Z-axis direction. The second test region region2 may be a region between the upper surface 200U of the first semiconductor device 200 and the first test region region1.

For example, when the first semiconductor device 200 includes a first layer formed on a substrate and a second layer formed on the first layer, the first test region region1 may include at least a portion of the first layer. Also, the second test region region2 may include at least a portion of the second layer. That is, the first test region region1 and the second test region region2 may overlap each other in the Z-axis direction.

In some embodiments, a Z-axis coordinate range of the unit region UR extending along the Z-axis direction may be included in the third range ZR (AU) and smaller than the third range ZR (AU). Therefore, the test system 100 may repeat a test several times to test the entire first semiconductor device 200.

Referring again to FIG. 1, the incident optics 110 may input a first beam L1 and a second beam L2 to the stage region SR.

The incident optics 110 may include a light source 111, a dispersion/birefringence optics 113, and a lens 115.

The light source 111 may emit a beam L0 to the dispersion/birefringence optics 113.

The dispersion/birefringence optics 113 may split the beam L0 received from the light source 111 into the first beam L1 and the second beam L2. The first beam L1 and the second beam L2 may be incident on the lens 115 substantially simultaneously. The lens 115 may be disposed above the stage region SR and may be separated from the stage region SR. In some embodiments, another component (e.g., a beam splitter) may further be provided between the dispersion/birefringence optics 113 and the lens 115 to input the first beam L1 and the second beam L2 to the lens 115.

In some embodiments, the dispersion/birefringence optics 113 may include a monochromator.

Figure 3:
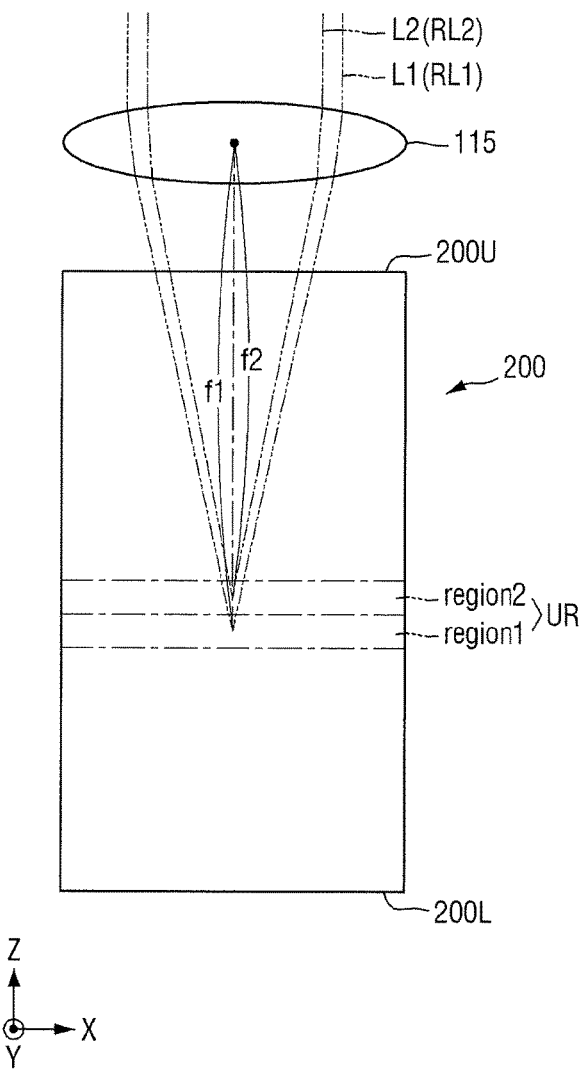
FIG. 3 is a diagram for explaining embodiments relating to a first beam and a second beam of FIG. 1.

FIG. 3 is a diagram for explaining embodiments relating to the first beam L1 and the second beam L2 of FIG. 1. For clarity of illustration, only the first semiconductor device 200 disposed on the stage 101 of the stage region SR, the lens 115, the first beam L1, and the second beam L2 are illustrated. FIG. 3 is a cross-sectional view taken along the line A-A' of the perspective view of the first semiconductor device 200 of FIG. 2B and may be a cross-sectional view on an X-Z plane. In addition, FIG. 3 may be a view for explaining a case where the dispersion/birefringence optics 113 includes a monochromator in some embodiments.

Referring to FIG. 3, in some embodiments according to the inventive concept, a first wavelength of the first beam L1 may be greater than a second wavelength of the second beam L2. A first focal length f1 of the first beam L1 may be greater than a second focal length f2 of the second beam L2. Therefore, the first beam L1 may be incident more deeply into the first semiconductor device 200 than the second beam L2 with respect to the upper surface 200U of the first semiconductor device 200.

The first beam L1 incident on the first semiconductor device 200 through the lens 115 may reach the first test region region1. On the other hand, since the second focal length f2 is less than the first focal length f1, the second beam L2 incident on the first semiconductor device 200 through the lens 115 may reach the second test region region2.

Since the first beam L1 and the second beam L2 are incident substantially simultaneously through the lens 115, the test system 100 according to the inventive concept can scan the first test region region1 and the second test region region2 substantially simultaneously during one test (that is, during the first test). Thus, the time used to test the first semiconductor device 200 can be reduced.

In the drawing, the beam L0 is illustrated as being split into two beams (the first beam L1 and the second beam L2). However, the inventive concept is not limited to this case. The beam L0 may be split into, e.g., three or more beams having different wavelengths by the monochromator. In this case, the three or more beams may have different focal lengths. Therefore, the three or more beams may be incident on the first test region region1, the second test region region2, and other regions overlapping each other along the Z-axis direction. That is, the three or more beams can reach different depths of the first semiconductor device 200 with respect to the upper surface 200U of the first semiconductor device 200. In this case, the test system 100 according to the inventive concept can substantially simultaneously scan regions of different depths of the first semiconductor device 200 in one test (e.g., during the first test). Thus, the time used to test the first semiconductor device 200 can be reduced.

The test system 100 according to embodiments of the inventive concept can reduce the time used to test the first semiconductor device 200 by inputting, substantially simultaneously, the first beam L1 and the second beam L2 having different focal lengths to the first semiconductor device 200. For example, when the first semiconductor device 200 includes a plurality of layers, the test system 100 may scan the layers substantially simultaneously using the first beam L1 and the second beam L2, thereby reducing the time used to perform a test for determining a defective region of the first semiconductor device 200.

A first reflected beam RL1 may be a beam obtained after the first beam L1 is reflected from the first test region1. A second reflected beam RL2 may be a beam obtained after the second beam L2 is reflected from the second test region region2. The first reflected beam RL1 may be reflected along the same path as the path along which the first beam L1 was incident on the first test region region1. The second reflected beam RL2 may be reflected along the same path as the path along which the second beam L2 was incident on the second test region region2.

The first reflected beam RL1 may include information about the first test region region1. The second reflected beam RL2 may include information about the second test region region2.

Referring again to FIG. 1, in some embodiments, the dispersion/bireftingence optics 113 may include a polarizer.

Figure 4:
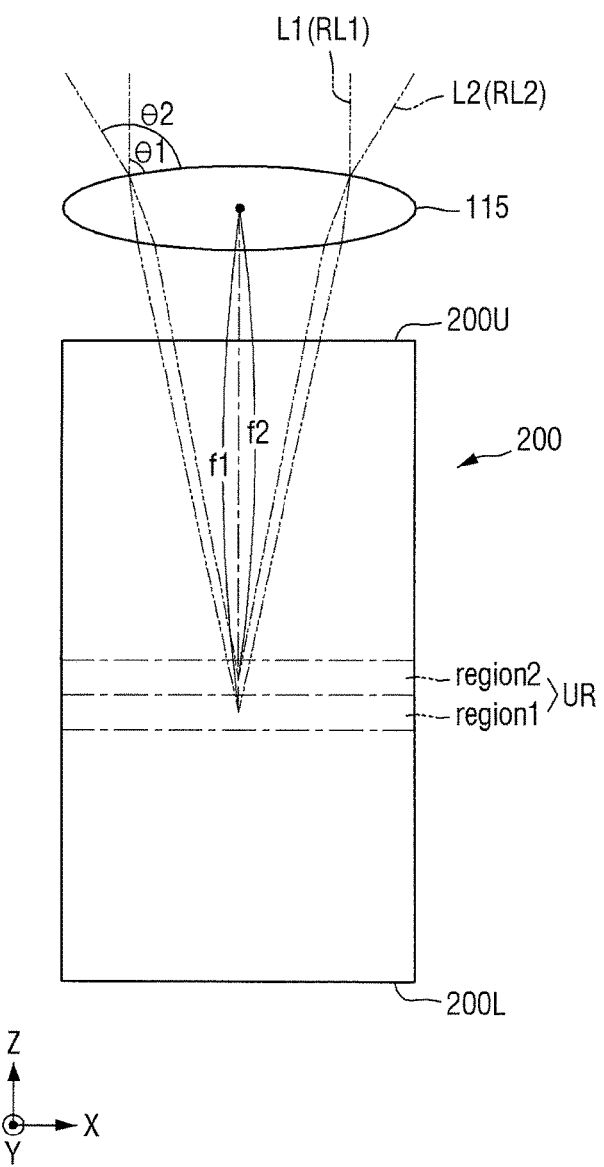
FIG. 4 is a diagram for explaining embodiments relating to the first beam and the second beam of FIG. 1.

FIG. 4 is a diagram for explaining embodiments relating to the first beam L1 and the second beam L2 of FIG. 1. For clarity of illustration, only the first semiconductor device 200 disposed on the stage 101 of the stage region SR, the lens 115, the first beam L1, and the second beam L2 are illustrated. FIG. 4 is a cross-sectional view taken along the line A-A' of the perspective view of the first semiconductor device 200 of FIG. 2B and may be a cross-sectional view on the X-Z plane. In addition, FIG. 4 may be a view for explaining a case where the dispersion/birefringence optics 113 includes a polarizer in some embodiments.

Referring to FIG. 4, in some embodiments according to the inventive concept, a first polarization direction of the first beam L1 may be different from a second polarization direction of the second beam L2, whereas the respective wavelengths of the first and seconds beams L1 and L2 can be the same. For example, the first beam L1 may be incident at a first angle $\theta 1$ to the lens 115. In addition, the second beam L2 may be incident at a second angle $\theta 2$ different from the first angle $\theta 1$ to the lens 115. Therefore, the first focal length f1 of the first beam L1 and the second focal length f2 of the second beam L2 may be different from each other. For example, the first focal length f1 may be greater than the second focal length f2.

The first beam L1 may reach the first test region region1. On the other hand, since the second focal length f2 is smaller than the first focal length f1, the second beam L2 incident on the first semiconductor device 200 through the lens 115 may reach the second test region region2. Since the first beam L1 and the second beam L2 are incident substantially simultaneously through the lens 115, the test system 100 according to some embodiments of the inventive concept can scan the first test region region1 and the second region region2 substantially simultaneously. Therefore, the time used to test the first semiconductor device 200 can be reduced.

The first reflected beam RL1 may be a beam obtained after the first beam L1 is reflected from the first test region region1. The second reflected beam RL2 may be a beam obtained after the second beam L2 is reflected from the second test region region2. The first reflected beam RL1 may be reflected along the same path as the path along which the first beam L1 was incident on the first test region region1. The second reflected beam RL2 may be reflected along the same path as the path along the second beam L2 was incident on the second test region region2.

The first reflected beam RL1 may include information about the first test region region1. The second reflected beam RL2 may include information about the second test region region2.

Referring again to FIG. 1, the first reflected beam RL1 and the second reflected beam RL2 may be incident on the light detector 120. The first reflected beam RL1 and the second reflected beam RL2 may be incident on the light detector 120 substantially simultaneously. The light detector 120 may separate the first reflected beam RL1 and the second reflected beam RL2 that are incident substantially simultaneously and input the separated first and second reflected beams RL1 and RL2 to the image processor 140.

Figure 5:
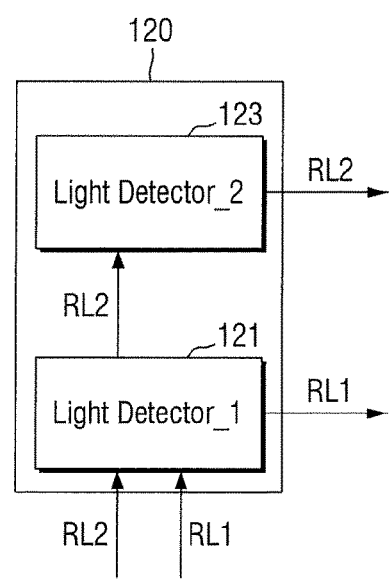
FIGS. 5 and 6 are block diagrams in some embodiments according to the inventive concept relating to a light detector of FIG. 1.
Figure 6:
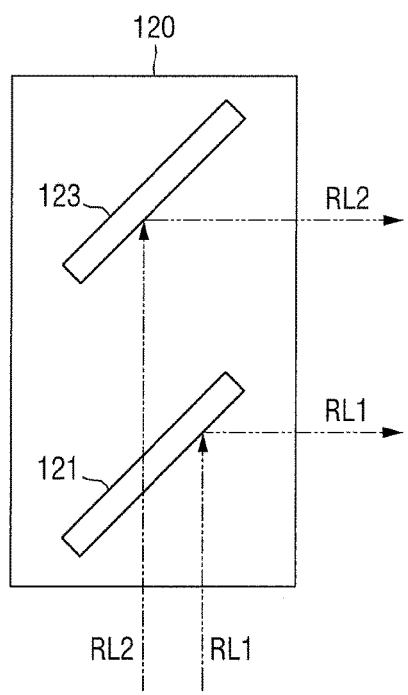

FIGS. 5 and 6 are block diagrams for explaining embodiments relating to the light detector 120 of FIG. 1.

Referring to FIG. 5, the light detector 120 may include a first light detector 121 and a second light detector 123.

The first light detector 121 may detect the first reflected beam RL1 among the first reflected beam RL1 and the second reflected beam RL2. The second light detector 123 may detect the second reflected beam RL2 among the first reflected beam RL1 and the second reflected beam RL2. For example, the second light detector 123 may detect the second reflected beam RL2 that passes through the first light detector 121.

In some embodiments, the first light detector 121 and the second light detector 123 may respectively detect beams having different wavelengths. In some embodiments, the first light detector 121 and the second light detector 123 may respectively detect beams having different polarization directions.

In some embodiments, each of the first light detector 121 and the second light detector 123 may include a beam splitter.

Referring to FIG. 6, both the first reflected beam RL1 and the second reflected beam RL2 may be incident on the first light detector 121 which is a beam splitter. The first light detector 121 may reflect only the first reflected beam RL1 and transmit the second reflected beam RL2. The transmitted second reflected beam RL2 may be reflected by the second light detector 123 which is another beam splitter.

Referring again to FIG. 1, each of the first reflected beam RL1 and the second reflected beam RL2 may be incident on the image processor 140.

In some embodiments, the test system 100 may further include a plurality of filters. For example, the first reflected beam RL1 and the second reflected beam RL2 may be incident on the filters, respectively. Each of the filters may remove noise contained in the first reflected beam RL1 or the second reflected beam RL2. In this case, reflected beams incident on the image processor 140 may be the filtered first reflected beam and the filtered second reflected beam.

The image processor 140 may receive the first reflected beam RL1 from the first light detector 121 and receive the second reflected beam RL2 from the second light detector 123. The image processor 140 may perform image processing using the first reflected beam RL1 and the second reflected beam RL2. The image processor 140 may generate a three-dimensional (3D) image I1 of the first semiconductor device 200. The 3D image I1 may be provided to each of the defect analyzer 150 and the sampler 160.

The defect analyzer 150 may compare the 3D image I1 with a reference 3D image to determine a defective region in the 3D image I1. Using the 3D image I1, the sampler 160 may determine a test region of a second semiconductor wafer that is to be tested next. The defect analyzer 150 and the sampler 160 are described herein in detail.

Figure 7:
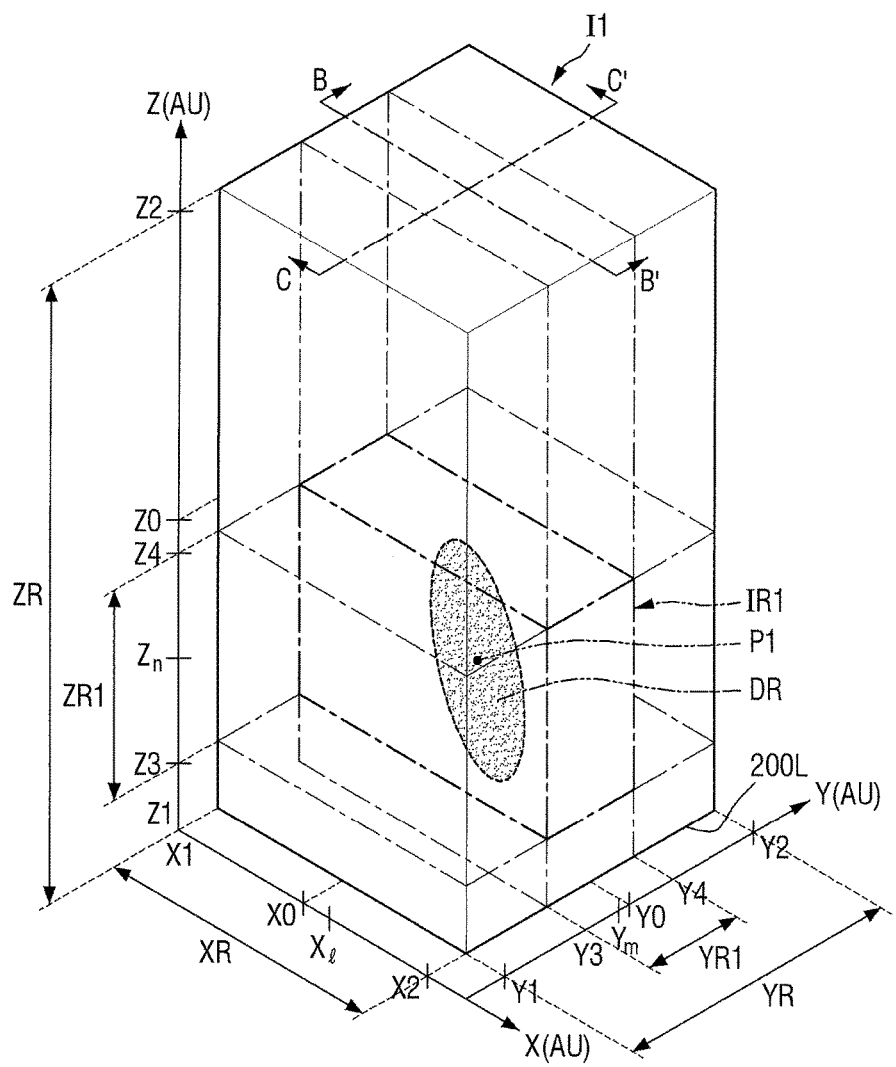
FIG. 7 illustrates a three-dimensional (3D) image output from an image processor of FIG. 1.
Figure 8:
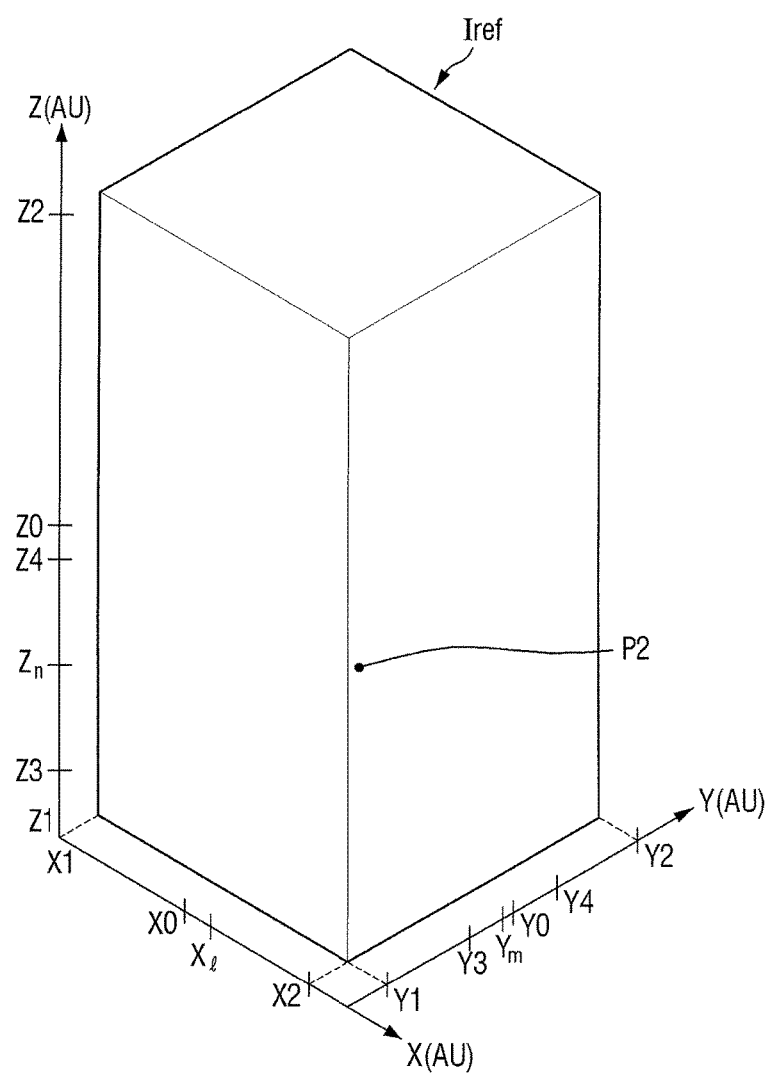
FIG. 8 is a diagram for explaining a defect analyzer of FIG. 1.

FIG. 7 illustrates the 3D image I1 output from the image processor 140 of FIG. 1. FIG. 8 is a diagram for explaining the defect analyzer 150 of FIG. 1.

Referring to FIGS. 7 and 8, the 3D image I1 of FIG. 7 may include information about the X-axis coordinate range (i.e., the first range XR), the Y-axis coordinate range (i.e., the second range YR) and the Z-axis coordinate range (i.e., the third range ZR) of the first semiconductor device 200. A reference 3D image Iref of FIG. 8 may have the same coordinate ranges as the X-axis coordinate range (i.e., the first range XR), the Y-axis coordinate range (i.e. the second range YR), and the Z-axis coordinate range (i.e., the third range ZR) of the first semiconductor device 200.

The reference 3D image Iref may be, for example, a 3D image of a semiconductor device formed in a region adjacent to region A of the first semiconductor wafer W1 described above with reference to FIG. 2A.

The defect analyzer 150 may arbitrarily set a plurality of reference points in the 3D image I1. Here, a plurality of reference points respectively corresponding to the reference points set in the 3D image I1 may also be set in the reference 3D image Iref. The defect analyzer 150 may calculate a difference value between the light intensity of each of the reference points in the 3D image I1 and the light intensity of each of the reference points in the reference 3D image Iref. The defect analyzer 150 may determine a region including a reference point whose difference value is larger than a predetermined value among the reference points in the 3D image I1 as a defective region DR.

In some embodiments, the predetermined value may be a value obtained by multiplying a constant by a height of the first semiconductor device 200 in the Z-axis direction. The constant may be, for example, an experimentally obtained value.

The defect analyzer 150 may set, for example, a first reference point P1 in the 3D image I1. Coordinates of the first reference point P1 may be $X_1$, $Y_m$, $Z_n$). $X_1$ may be included in the X-axis coordinate range (i.e., the first range XR) of the first semiconductor device 200. $Y_m$ may be included in the Y-axis coordinate range (i.e., the second range YR) of the first semiconductor device 200. $Z_n$ may be included in the Z-axis coordinate range (i.e., the third range ZR) of the first semiconductor device 200.

The defect analyzer 150 may set a second reference point P2 in the pre-stored reference 3D image Iref. The second reference point P2 may be a reference point corresponding to the first reference point P1. That is, coordinates of the second reference point P2 may also be ($X_1$, $Y_m$, $Z_n$).

The defect analyzer 150 may measure light intensity at the first reference point P1 and light intensity at the second reference point P2. When a difference value between the light intensity at the first reference point P1 and the light intensity at the second reference point P2 is greater than the predetermined value, the defect analyzer 150 may determine a region including the first reference point P1 as the defective region DR.

Figure 9:
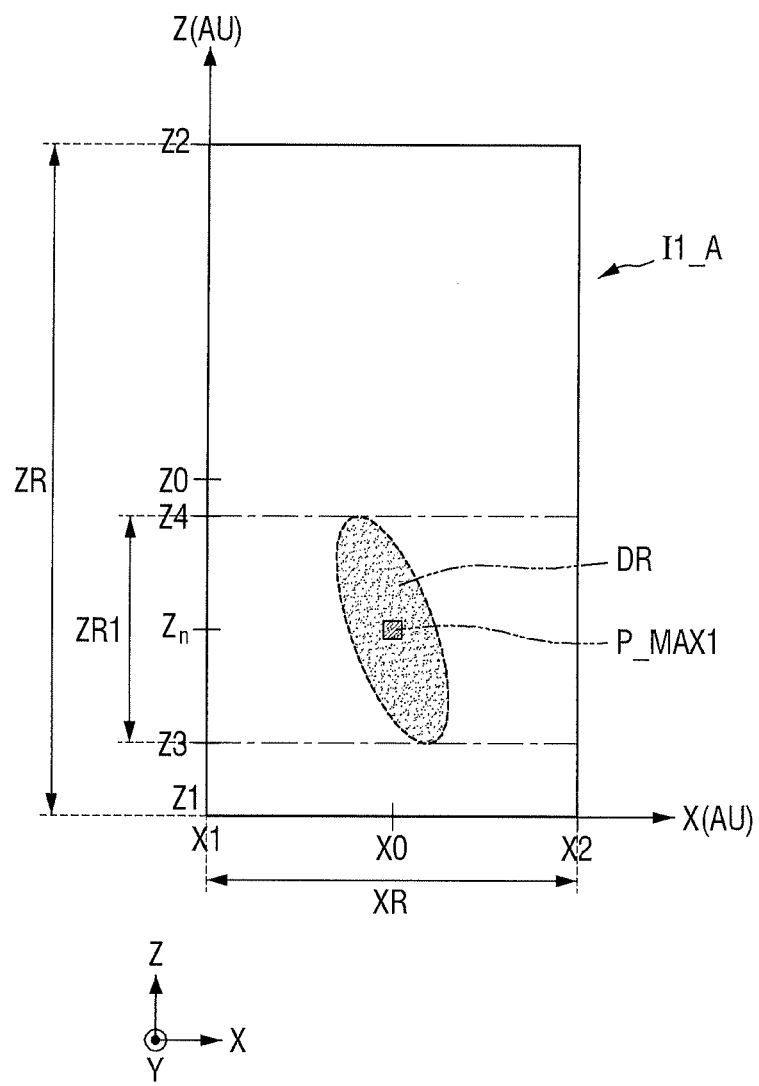
FIGS. 9 and 10 are diagrams for explaining a sampler of FIG. 1.
Figure 10:
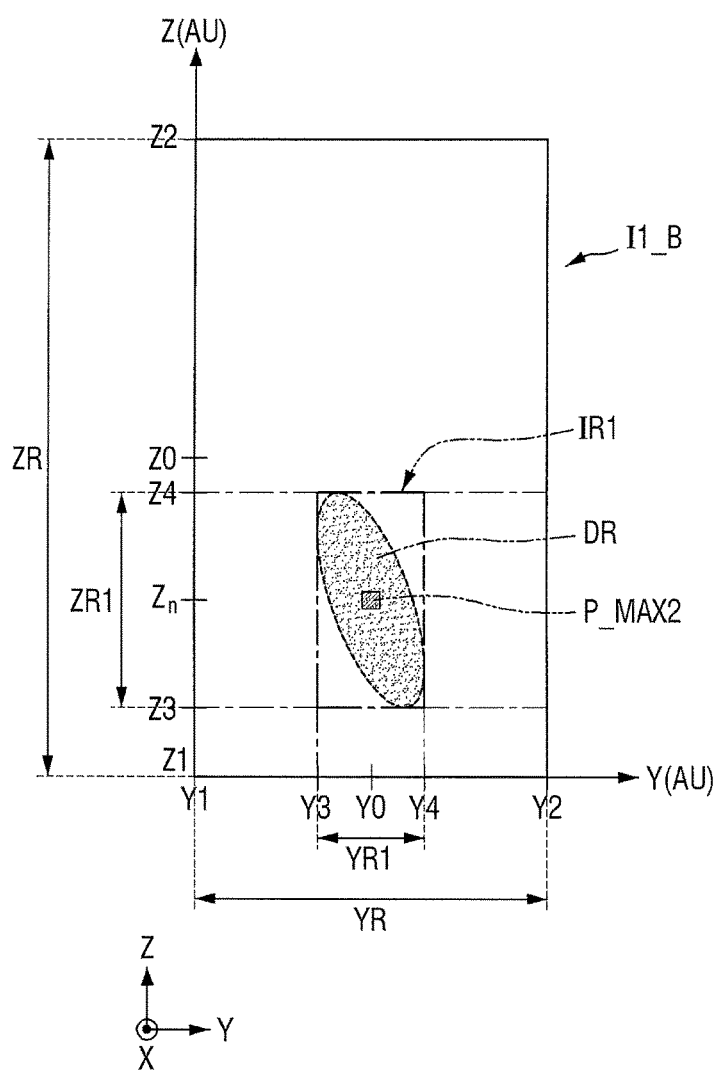

FIGS. 9 and 10 are diagrams for explaining the sampler 160 of FIG. 1. A first partial image I1_A of FIG. 9 may be an image on the X-Z plane obtained by cutting the 3D image I1 of FIG. 7 along the line B-B'. A second partial image I1_B of FIG. 10 may be an image on a Y-Z plane obtained by cutting the 3D image I1 of FIG. 7 along the line C-C'.

Referring to FIGS. 7, 9 and 10, the sampler 160 may detect a first image region IR1 and a second image region in the 3D image I1. In some embodiments, the sampler 160 may receive information about the defective region DR determined by the defect analyzer 150. The information about the defective region DR may include information about an X-axis coordinate range, a Y-axis coordinate range and a Z-axis coordinate range of the defective region DR.

The first image region IR1 may be a region including the defective region DR. The first image region IR1 may include, for example, a pixel having maximum light intensity among a plurality of pixels included in the 3D image I1.

Specifically, in the first partial image I1_A of FIG. 9, the light intensity of the defective region DR may be greater than those of other regions excluding the defective region DR. Of a plurality of pixels included in the first partial image I1_A, a pixel having the maximum light intensity may be a first pixel P_MAX1. The sampler 160 may set the Z-axis range (Z3 (AU) to Z4 (AU)) of the defective region DR including the first pixel P_MAX1 to a first Z-axis range ZR1 of the first image region IR1.

In addition, in the second partial image I1_B of FIG. 10, the light intensity of the defective region DR may be greater than those of other regions outside the defective region DR. Of a plurality of pixels included in the second partial image I1_B, a pixel having the maximum light intensity may be a second pixel P_MAX2. The sampler 160 may set the Y-axis range (Y3 (AU) to Y4 (AU)) of the defective region DR including the second pixel P_MAX2 to a first Y-axis coordinate range YR1 of the first image region IR1.

That is, the first image region IR1 may extend along the X-axis direction by the first range XR, extend along the Y-axis direction by the first Y-axis coordinate range YR1, and extend along the Z-axis direction by the first Z-axis coordinate range ZR1.

The second image region may be a region outside the first image region IR1 in the 3D image I1.

The first image region IR1 may be a test region of a next semiconductor wafer to be tested after the first semiconductor wafer W1.

Referring again to FIG. 1, the sampler 160 may output sampled test region information SI. The sampled test region information SI may include information about the first image region IR1.

The controller 170 may receive the sampled test region information SI from the sampler 160. The controller 170 may provide the test system 100 with an instruction TI for setting a test region of a second semiconductor wafer W2 based on the sampled test region information SI.

Figure 11A:
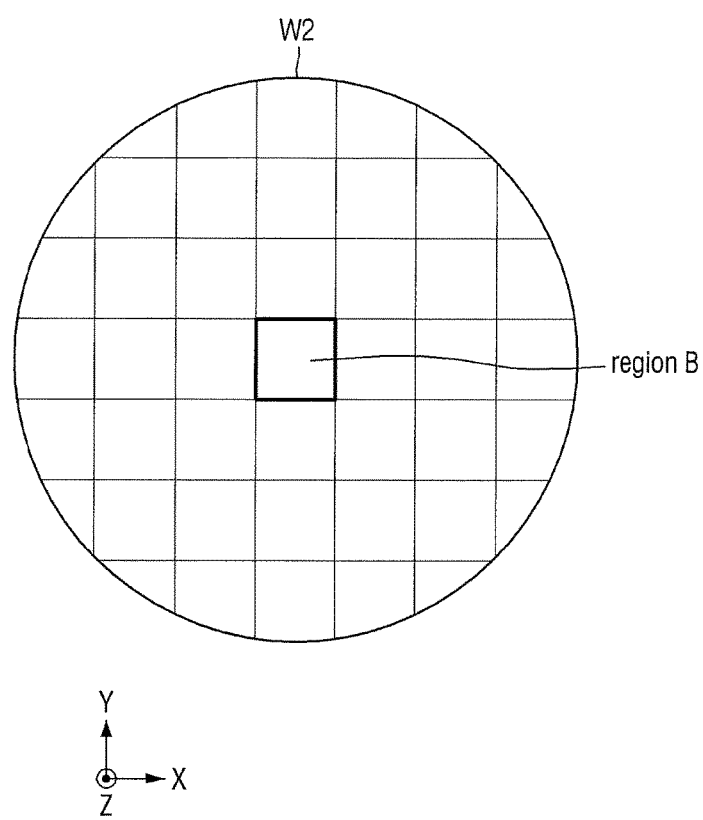
FIG. 11A illustrates a second semiconductor wafer on which the test system of FIG. 1 performs a second test.
Figure 11B:
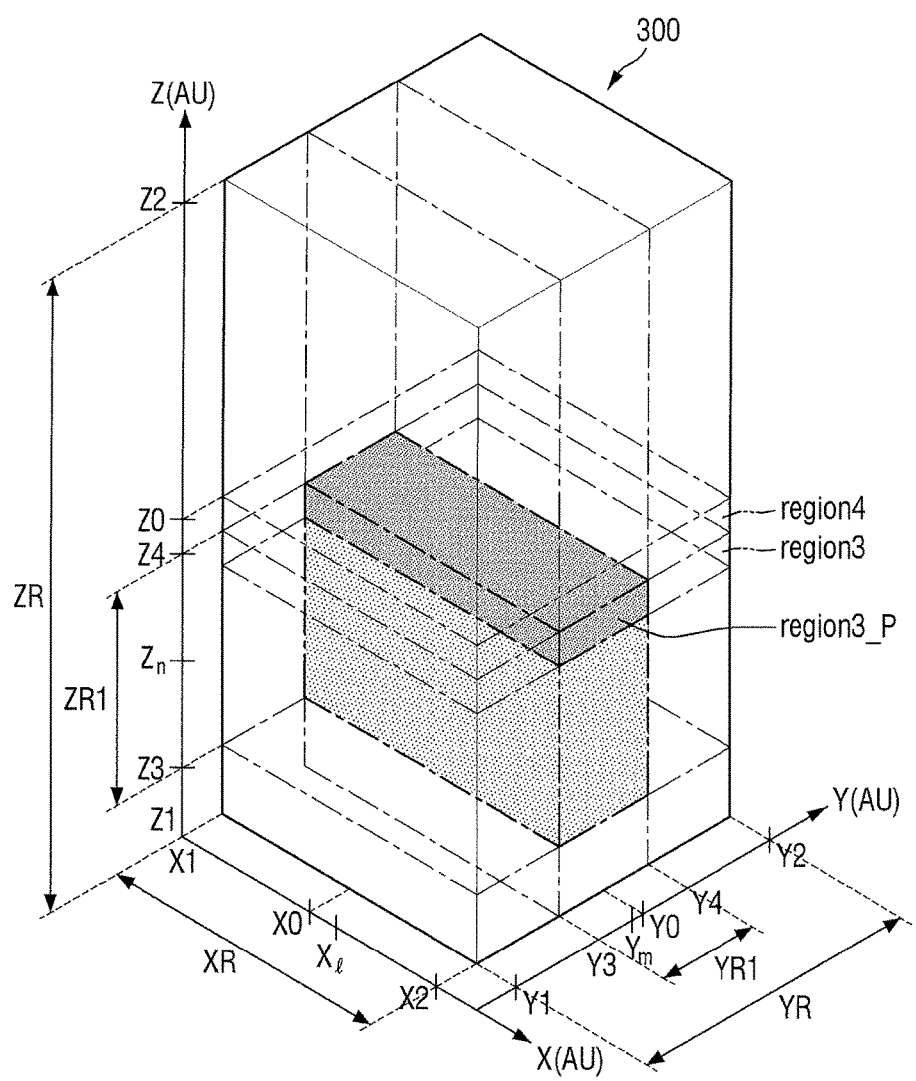
FIG. 11B is a diagram for explaining embodiments relating to a test region on which the second test is performed.

FIG. 11A illustrates the second semiconductor wafer W2 on which the test system 100 of FIG. 1 performs a second test. FIG. 11B is a diagram for explaining embodiments relating to a test region on which the second test is performed.

Referring to FIGS. 11A and 11B, after completing the first test on the first semiconductor wafer W1 described above with reference to FIG. 2A, the test system 100 may perform the second test on the second semiconductor wafer W2. On the stage 101 of FIG. 1, the second semiconductor wafer W2 may replace the first semiconductor wafer W1.

Region B of the second semiconductor wafer W2 may be a region corresponding to region A of the first semiconductor wafer W1 described above with reference to FIG. 2A. A second semiconductor device 300 may be a semiconductor device formed on region B of the second semiconductor wafer W2.

In the second test, the test system 100 may scan the second semiconductor device 300 by the first range XR in the X-axis direction, by the first Y-axis coordinate range YR1 in the Y-axis direction, and by the first Z-axis coordinate range ZR1 in the Z-axis direction. That is, unlike in the first test, in the second test, a specific region (e.g., a region corresponding to the first image region IR1) of the second semiconductor device 300 may be scanned.

Specifically, a third test region region3 may be a region corresponding to the first test region region1 described above with reference to FIG. 2B. A fourth test region region4 may be a region corresponding to the second test region region2 described above with reference to FIG. 2B.

A Z-axis range of the third test region region3 may be included in the first Z-axis coordinate range ZR1. A Z-axis range of the fourth test region region4 may not be included in the first Z-axis coordinate range ZR1. In this case, only the third test region region3 may be considered as a test region of the second semiconductor device 300 in the second test. Further, of a Y-axis range of the third test region region3, only a region within the first Y-axis coordinate range YR1 may be considered as the test region in the second test. Consequently, a region region3_P of the third test region region3 may be the test region in the second test.

The test system 100 according to the technical spirit of the inventive concept can reduce the time used to test the first and second semiconductor devices 200 and 300 by performing the first test on the entire region of the first semiconductor device 200 (see FIG. 2B) and then performing the second test on a region (the region region3_P of the third test region region3 of FIG. 11B) of the second semiconductor device 300 (see FIG. 11B) which may be more targeted than the first test.

The various embodiments relating to all or some of the functions of the image processor 140, the defect analyzer 150, and the sampler 160 described above may be implemented as operations in a recording medium readable by a computer or a similar device using software, hardware or a combination of the software and the hardware. According to embodiments of the inventive concept, data on the first reflected beam RL1 and the second reflected beam RL2 may be transmitted as input data to the software or the hardware.

According to software implementation, embodiments such as procedures or functions may be implemented together with separate software modules that perform at least one function or operation. The software codes can be implemented by a software application written in an appropriate programming language. It will be further understood that the blocks shown in the FIGs. can represent support for the software codes/operations described herein.

Hereinafter, a test method according to embodiments will be described. For clarity, a description of components and features described above will be omitted.

Figure 12:
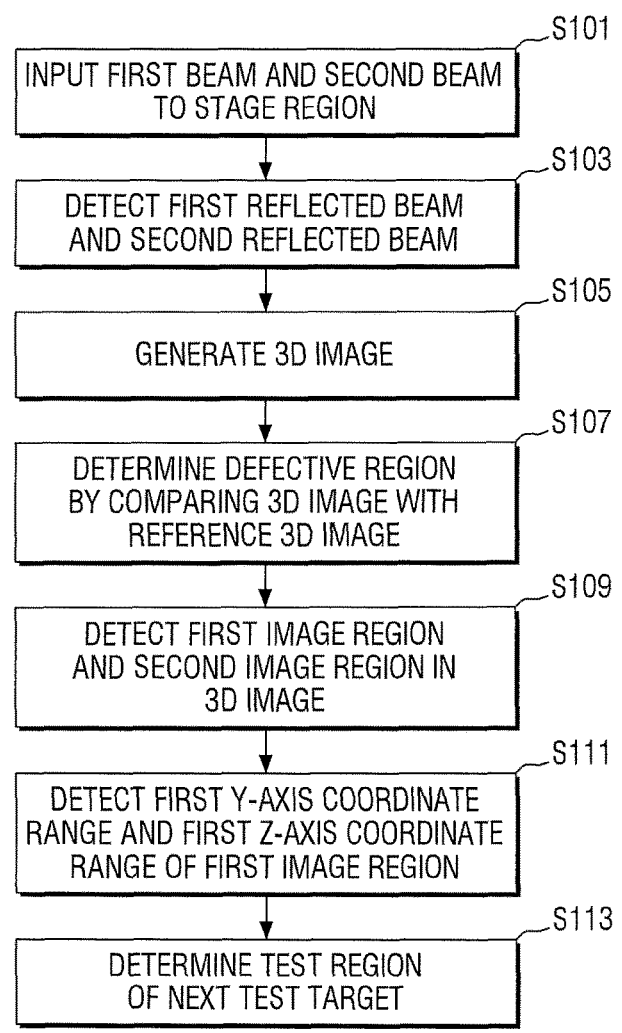
FIG. 12 is a flowchart illustrating a test method according to embodiments.

FIG. 12 is a flowchart illustrating a test method according to embodiments of the inventive concept.

Referring to FIG. 12, a first beam and a second beam may be input to a stage region (operation S101).

As described above with reference to FIGS. 1, 3 and 4, the inputting of the first beam and the second beam to the stage region may include receiving a beam L0 (see FIG. 1) from a light source 111 (see FIG. 1) and splitting the beam L0 into a first beam L1 (see FIGS. 1, 3 and 4) and a second beam L2 (see FIGS. 1, 3 and 4). In some embodiments, a first wavelength of the first beam L1 may be greater than a second wavelength of the second beam L2. Alternatively, in some embodiments, a first polarization direction of the first beam L1 may be different from a second polarization direction of the second beam L2, whereas the respective wavelengths of the first and second beams L1, L2 maybe the same.

The first beam L1 (see FIGS. 1, 3 and 4) may have a first focal length f1 (see FIGS. 3 and 4). The second beam L2 (see FIGS. 1, 3 and 4) may have a second focal length f2 (see FIGS. 3 and 4) less than the first focal length f1.

In the stage region SR (see FIG. 1), a test target (W1 in FIGS. 1 and 2A) may be placed. In this case, the first beam L1 (see FIGS. 1, 3 and 4) and the second beam L2 (see FIGS. 1, 3 and 4) may be input to the test target (W1 in FIGS. 1 and 2A).

In operation S103, a first reflected beam RL1 and a second reflected beam RL2 reflected from the stage region SR may be detected.

Specifically, operation S103 may include detecting the first reflected beam RL1 among the first reflected beam RL1 and the second reflected beam RL2 reflected from the stage region SR and detecting the second reflected beam RL2 among the first reflected beam RL1 and the second reflected beam RL2 reflected from the stage region SR.

The first reflected beam RL1 (see FIGS. 1, 3, and 4) may be a beam obtained after the first beam L1 (see FIGS. 1, 3, and 4) is reflected from the stage region SR (see FIG. 1). Specifically, the first reflected beam RL1 (see FIGS. 1, 3 and 4) may be a beam obtained after the first beam L1 (see FIGS. 1, 3 and 4) is reflected from a first test region region1 (see FIGS. 2B, 3 and 4).

The second reflected beam RL2 (see FIGS. 1, 3 and 4) may be a beam obtained after the second beam L2 (see FIGS. 1, 3 and 4) is reflected from the stage region SR (see FIG. 1). Specifically, the second reflected beam RL2 (see FIGS. 1, 3 and 4) may be a beam obtained after the second beam L2 (see FIGS. 1, 3 and 4) is reflected from a second test region region2 (see FIGS. 2B, 3 and 4).

The first reflected beam may be detected by a first light detector 121 (see FIG. 5), and the second reflected beam may be detected by a second light detector 123 (see FIG. 5).

In operation S105, a 3D image may be generated.

Specifically, a first image may be generated from the first reflected beam, and a second image may be generated from the second reflected beam. The first image may be an image of the first test region region1 (see FIGS. 2B, 3 and 4) of a first semiconductor device. The second image may be an image of the second test region region2 (see FIGS. 2B, 3 and 4) of the first semiconductor device.

A 3D image I1 (see FIGS. 1 and 7) may be generated using the first image and the second image. For example, the 3D image I1 (see FIGS. 1 and 7) may be generated by combining the first image and the second image.

In operation S107, a defective region may be determined by comparing the 3D image with a reference 3D image.

Specifically, as described above with reference to FIGS. 7 and 8, a defective region DR (see FIG. 7) may be determined using a difference value between a reference point in the 3D image I1 (see FIG. 7) and a reference point in a reference 3D image Iref (see FIG. 8). The 3D image I1 (see FIG. 7) may include information about an X-axis coordinate range, a Y-axis coordinate range and a Z-axis coordinate range of an object (the first semiconductor device 200 of FIG. 2B) whose 3D image has been extracted.

In operation S109, a first image region and a second image region may be detected in the 3D image using information from the defect analyzer 150 related to the coordinates of the defective region in the 3D image.

The first image region IR1 (see FIGS. 7, 9 and 10) may include, for example, the defective region DR (see FIG. 7). The light intensity of the defective region DR may be higher than those of other regions outside the defective region DR. Also, the first image region may include a pixel (P_MAX1 in FIG. 9 and P_MAX2 in FIG. 10) having maximum light intensity among a plurality of pixels included in the 3D image I1 (see FIGS. 1 and 7).

In operation S111, a first Y-axis coordinate range YR1 (see FIG. 7) and a first Z-axis coordinate range ZR1 (see FIG. 7) of the first image region may be detected.

In operation S113, a test region of a next test target may be determined.

Specifically, the test region of the next test target may be a region corresponding to the first image region.

The next test target may be, for example, a second semiconductor wafer W2 described above with reference to FIG. 11A. As described above with reference to FIG. 11B, the test region of the next test target may be a region region3_P corresponding to the first image region.

Hereinafter, a method of fabricating a semiconductor device according to embodiments will be described. For clarity, a description of components and features described above will be omitted.

Figure 13:
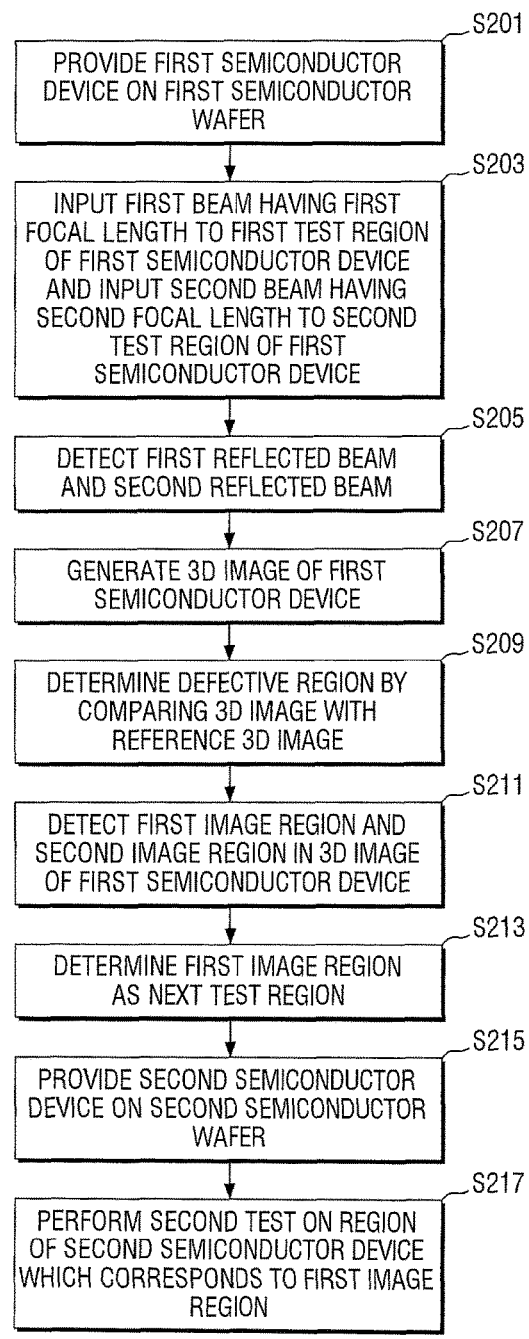
FIG. 13 is a flowchart illustrating a method of fabricating a semiconductor device according to embodiments.

FIG. 13 is a flowchart illustrating a method of fabricating a semiconductor device according to embodiments.

Referring to FIG. 13, in operation S201, a first semiconductor device on a first semiconductor wafer may be provided. The first semiconductor device may include at least one layer. For example, the first semiconductor device may include a first layer and a second layer formed on the first layer.

In operation S203, a first beam may be incident on a first test region of the first semiconductor device, and a second beam may be incident on a second test region of the first semiconductor device. The first test region and the second test region may be scanned by the first beam and the second beam, respectively. Here, the first test region may include at least a portion of the first layer, and the second test region may include at least a portion of the second layer. In the method of fabricating a semiconductor device according to the inventive concept, a first test may be performed substantially simultaneously on the first layer and the second layer.

As described above with reference to FIGS. 2A and 2B, the first test region and the second test region may be regions vertically overlapping each other with respect to the Z-axis direction. That is, the second test region may be a region between an upper surface of the first semiconductor device and the first test region.

As described above with reference to FIGS. 3 and 4, the first beam may have a first focal length f1, and the second beam L2 may have a second focal length f2 less than the first focal length f1.

In operation S205, a first reflected beam RL1 and a second reflected beam RL2 may be detected. As described above with reference to FIGS. 1 and 5, the first reflected beam RL1 and the second reflected beam RL2 reflected from the first semiconductor device may be detected separately.

In operation S207, a 3D image of the first semiconductor device may be generated. The 3D image may include information about an X-axis coordinate range, a Y-axis coordinate range, and a Z-axis coordinate range of the first semiconductor device, as described with reference to FIG. 7.

In operation S209, as described above with reference to FIGS. 7 and 8, a defective region DR of the first semiconductor device may be determined by comparing the 3D image with a reference 3D image. Accordingly, the first test on the first semiconductor device may be terminated. In other words, the first test on the first semiconductor device may include operations S201, S203, S205, S207 and S209.

In operation S211, a first image region and a second image region of the 3D image may be detected as described above with reference to FIGS. 7, 9 and 10.

In operation S213, the first image region may be determined as a test region of a next test target. Then, in operation S215, a second semiconductor device on a second semiconductor wafer may be provided. The second semiconductor device may include at least one layer.

In operation S217, a second test may be performed on a region (e.g., a region region3_P of a third test region in FIG. 11B) corresponding to the first image region, as described above with reference to FIGS. 11A and 11B.

The performing of the second test may include inputting the first beam to the region (e.g., the region region3_P of the third test region in FIG. 11B) corresponding to the first image region. A first reflected beam obtained after the first beam is reflected from the region (e.g., the region region3_P of the third test region in FIG. 11B) corresponding to the first image region may be detected. By using the first reflected beam, a 3D image of the region (e.g., the region region3_P of the third test region in FIG. 11B) corresponding to the first image region of the second semiconductor device may be generated.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims. It is therefore desired that the present embodiments be considered in all respects as illustrative and not restrictive, reference being made to the appended claims.

What is claimed is:

1. A test system comprising:
    an incident optics configured to provide a first beam having a first focal length and a second beam having a second focal length that is less than the first focal length;
    a stage region configured to support a semiconductor wafer, the stage region positioned to receive the first and second beams and to provide a first reflected beam and a second reflected beam to the incident optics responsive to the first and second beams;
    a first light detector configured to detect the first reflected beam among the first and second reflected beams reflected from the stage region to the first light detector through the incident optics;
    a second light detector configured to detect the second reflected beam among the first and second reflected beams reflected from the stage region to the second light detector through the incident optics; and
    an image processor configured to receive the first reflected beam from the first light detector and the second reflected beam from the second light detector and configured to generate a three-dimensional (3D) image based on the first and second reflected beams provided by the first and second light detectors, respectively, wherein the 3D image comprises information about an x-axis coordinate range, a y-axis coordinate range and a z-axis coordinate range; and
    a sampler configured to receive the 3D image and to detect a first image region and a second image region in the 3D image, to detect a first y-axis coordinate range and a first z-axis coordinate range of the first image region, and to determine a region having the x-axis coordinate range, the first y-axis coordinate range and the first z-axis coordinate range as a test region, wherein the first image region includes a pixel having maximum light intensity among a plurality of pixels included in the 3D image.

2. The test system of claim 1, wherein the incident optics comprises:
    a light source configured to emit a light beam;
    a dispersion optics positioned to receive the light beam and configured to split the light beam into the first beam with a first wavelength and into the second beam with a second wavelength; and
    a lens spaced apart from the stage region and positioned to receive the first and second beams and the first and second reflected beams, wherein the first wavelength of the first beam is greater than the second wavelength of the second beam.

3. The test system of claim 1, wherein the incident optics comprises:
    a light source configured to emit a light beam;
    a birefringence optics positioned to receive the light beam and configured to split the light beam into the first beam with a first direction of polarization and into the second beam with a second direction of polarization; and
    a lens spaced apart from the stage region and positioned to receive the first and second beams and the first and second reflected beams, wherein the first direction of polarization and the second direction of polarization are in different directions.

4. The test system of claim 1, wherein the first light detector comprises a beam splitter which reflects the first reflected beam toward the image processor and passes the second reflected beam away from the image processor.

5. The test system of claim 1, further comprising:
    a defect analyzer configured to receive the 3D image and to determine a difference value between light intensity at a first reference point in the 3D image and light intensity at a second reference point corresponding to the first reference point in a reference 3D image and configured to determine a region comprising the first reference point as a defective region when the difference value is greater than a predetermined value.

6. A method comprising:
    providing a first semiconductor wafer;
    performing a first test on the first semiconductor wafer, wherein the performing the first test comprises:
        providing a first beam with a first focal length to a first test region of the first semiconductor wafer to provide a first reflected beam from the first test region responsive to the first beam;
        providing a second beam with a second focal length less than the first focal length to a second test region of the first semiconductor wafer to provide a second reflected beam from the second test region responsive to the second beam, wherein the second test region is disposed between a surface of the first semiconductor wafer and the first test region;
        detecting the first reflected beam and the second reflected beam among beams reflected from the first semiconductor wafer; and
        generating a 3D image using the first reflected beam and the second reflected beam,
    wherein the first semiconductor wafer comprises a first layer and a second layer on the first layer, wherein the first test region comprises at least a portion of the first layer, the second test region comprises at least a portion of the second layer, and wherein performing the first test comprises testing the first layer and the second layer substantially simultaneously.

7. The method of claim 6 wherein providing the first beam comprises receiving a light beam from a light source and splitting the light beam into the first beam with a first wavelength and the second beam with a second wavelength, wherein the first wavelength is greater than the second wavelength.

8. The method of claim 6, wherein providing the first beam comprises receiving a light beam from a light source and splitting the light beam into the first beam with a first direction of polarization and the second beam with a second direction of polarization, wherein the first direction of polarization is different from the second direction of polarization.

9. The method of claim 6, further comprising:
providing a second semiconductor wafer;
determining a test region of the second semiconductor wafer;
performing a second test on the second semiconductor wafer,
wherein determining the test region of the second semiconductor wafer comprises:
- detecting a first image region and a second image region in the 3D image which comprises information about an x-axis coordinate range, a y-axis coordinate range and a z-axis coordinate range of the first semiconductor wafer;
- detecting a first y-axis coordinate range and a first z-axis coordinate range of the first image region; and
- determining a region having the x-axis coordinate range, the first y-axis coordinate range and the first z-axis coordinate range as the test region of the second semiconductor wafer.

10. The method of claim 9, wherein the second semiconductor wafer comprises a third test region corresponding to the first test region and a fourth test region corresponding to the second test region, and performing the second test on the second semiconductor wafer comprises:
providing the first beam to a region of the third test region of the second semiconductor wafer, wherein the region of the third test region comprises the x-axis coordinate range, the first y-axis coordinate range and the first z-axis coordinate range.

11. The method of claim 9, wherein the first image region includes a pixel having a maximum light intensity among a plurality of pixels included in the 3D image.

12. The method of claim 6, wherein performing the first test on the first semiconductor wafer further comprises:
determining a region of the first semiconductor wafer which corresponds to a first reference point as a defective region of the first semiconductor wafer when a difference value between light intensity at the first reference point in the 3D image and light intensity at a second reference point corresponding to the first reference point in a reference 3D image is greater than a predetermined value.

13. A test method comprising:
providing a first beam having a first focal length and a second beam having a second focal length that is less than the first focal length to a stage region to provide a first reflected beam and a second reflected beam from the stage region;
detecting the first reflected beam among the first reflected beam and the second reflected beam reflected from the stage region;
detecting the second reflected beam among the first reflected beam and the second reflected beam reflected from the stage region;
generating a first image from the first reflected beam;
generating a second image from the second reflected beam; and
combining the first image and the second image to provide a 3D image, wherein the 3D image comprises information about an x-axis coordinate range, a y-axis coordinate range and a z-axis coordinate range;
detecting a first image region and a second image region in the 3D image;
detecting a first y-axis coordinate range and a first z-axis coordinate range of the first image region; and
determining a region having the x-axis coordinate range, the first y-axis coordinate range and the first z-axis coordinate range as a test region.

14. The test method of claim 13, wherein providing the first beam having a first focal length and the second beam having the second focal length comprises:
emitting a light beam from a light source; and
splitting the light beam into the first beam having a first wavelength and the second beam having a second wavelength, wherein the first wavelength is greater than the second wavelength.

15. The test method of claim 13, wherein providing the first beam having a first focal length and the second beam having the second focal length comprises:
emitting a light beam from a light source; and
splitting the light beam into the first beam and the second beam, wherein the first beam has a first direction of polarization and the second beam has second direction of polarization that is different from the first direction of polarization.

16. The test method of claim 13, wherein the first image region comprises a pixel having a maximum light intensity among a plurality of pixels included in the 3D image.

17. The test method of claim 13, further comprising:
comparing the 3D image with a reference 3D image to determine a defective region in the 3D image.

* * * * *